(12) United States Patent
Sturtevant et al.

(10) Patent No.: US 10,352,907 B2
(45) Date of Patent: Jul. 16, 2019

(54) HIGH-TEMPERATURE, HIGH PRESSURE ACOUSTIC RESONANCE CELL

(71) Applicant: Triad National Security, LLC, Los Alamos, NM (US)

(72) Inventors: Blake T. Sturtevant, Los Alamos, NM (US); Cristian Pantea, Los Alamos, NM (US); Dipen N. Sinha, Los Alamos, NM (US)

(73) Assignee: Los Alamos National Security, LLC, Los Alamos, NM (US)

(*) Notice: Subject to any disclaimer, the term of this patent is extended or adjusted under 35 U.S.C. 154(b) by 92 days.

(21) Appl. No.: 15/039,365

(22) PCT Filed: Nov. 26, 2014

(86) PCT No.: PCT/US2014/067721
§ 371 (c)(1),
(2) Date: May 25, 2016

(87) PCT Pub. No.: WO2015/081264
PCT Pub. Date: Jun. 4, 2015

(65) Prior Publication Data
US 2017/0108471 A1  Apr. 20, 2017

Related U.S. Application Data

(60) Provisional application No. 61/909,304, filed on Nov. 26, 2013.

(51) Int. Cl.
*G01N 29/22* (2006.01)
*G01N 29/036* (2006.01)

(52) U.S. Cl.
CPC ......... *G01N 29/227* (2013.01); *G01N 29/036* (2013.01); *G01N 29/222* (2013.01); *G01N 29/228* (2013.01); *G01N 2291/011* (2013.01)

(58) Field of Classification Search
CPC .. G01N 29/227; G01N 29/036; G01N 29/222; G01N 29/228
(Continued)

(56) References Cited

U.S. PATENT DOCUMENTS 5,235,235 A    8/1993  Martin et al.
5,501,098 A *  3/1996  Cadet ............... G01N 29/024
                                                    73/24.01
(Continued)

OTHER PUBLICATIONS

PCT International Search Report, Application No. PCT/US2014/067721, dated Nov. 26, 2014 10 total pages.

*Primary Examiner* — Tarun Sinha
(74) *Attorney, Agent, or Firm* — Samuel M. Freund; Cochran Freund & Young LLC

(57) ABSTRACT

A compact, rugged and portable measurement cell design for the determination of sound speed in fluids at temperatures up to 250° C. and pressures up to 3,000 psi is described. Swept Frequency Acoustic Interferometry measurement for liquid sound speed determinations in liquids up to 250° C. is of both fundamental interest, as in the case of basic equations of state, and applied interest, such as for characterizing geothermal or petroleum down hole environments. Representative sound speeds for water, as a function of temperature and pressure, are in agreement with an internationally accepted standard for the sound speed of water.

18 Claims, 7 Drawing Sheets

(58) Field of Classification Search
USPC .......................................................... 73/579
See application file for complete search history.

(56) References Cited

U.S. PATENT DOCUMENTS

| | | | |
|---|---|---|---|
| 8,120,500 B2 | 2/2012 | Tokhtuev et al. | |
| 2003/0053915 A1* | 3/2003 | Keilman | F04B 17/00 |
| | | | 417/322 |
| 2008/0280371 A1 | 11/2008 | Anilkumar et al. | |
| 2010/0097892 A1* | 4/2010 | Aughton | G01F 23/2962 |
| | | | 367/99 |
| 2013/0167622 A1 | 7/2013 | Frivik | |
| 2014/0338423 A1* | 11/2014 | Buckland | G01N 29/022 |
| | | | 73/24.01 |

* cited by examiner

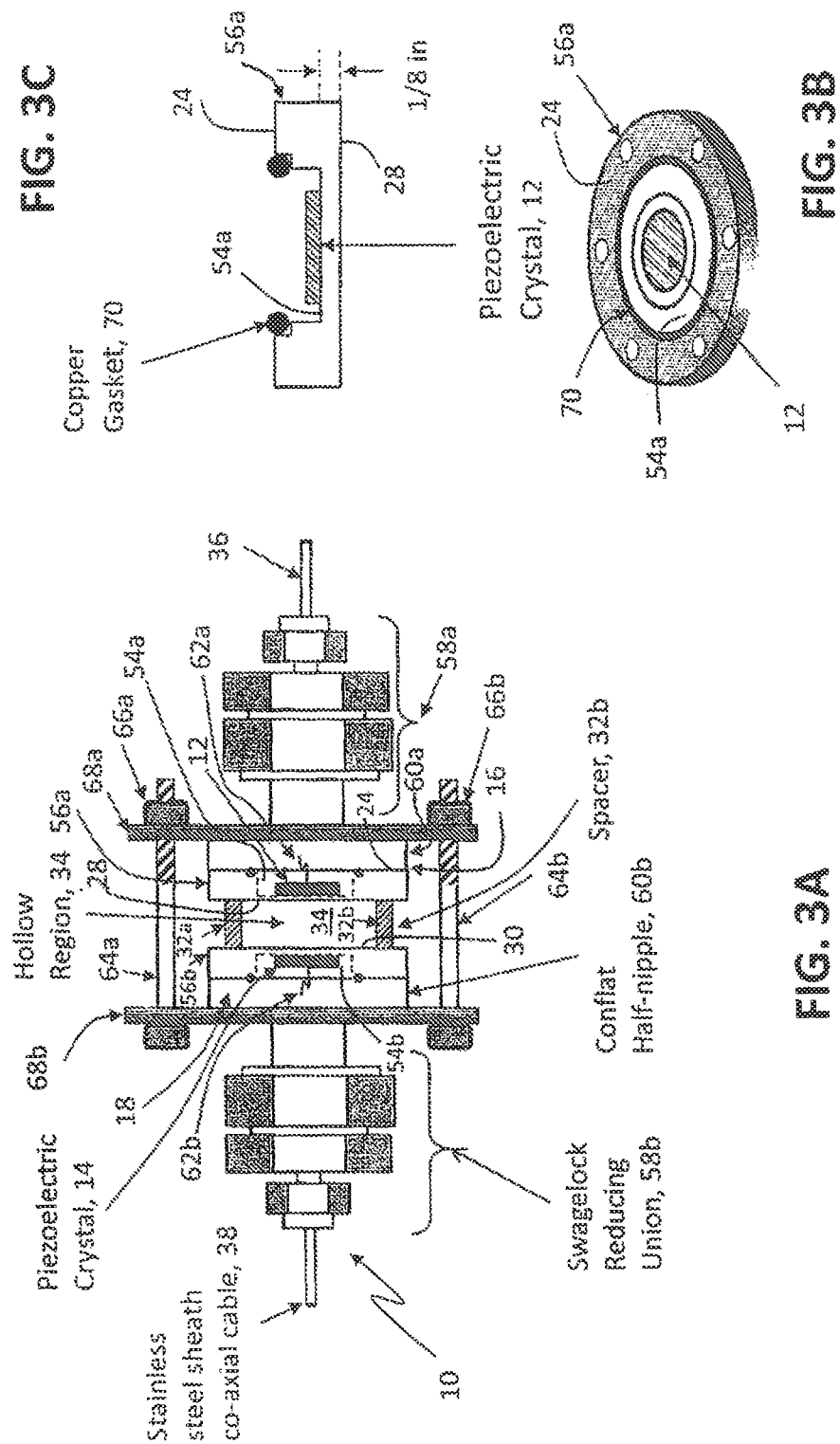

HIGH-TEMPERATURE, HIGH PRESSURE ACOUSTIC RESONANCE CELL

CROSS-REFERENCE TO RELATED APPLICATIONS

The present application is a National Phase application of PCT Patent Application Ser. No. PCT/US2014/067721U for "High-Temperature, High Pressure Acoustic Resonance Cell" by Blake T. Sturtevant et al., filed on Nov. 26, 2014, which claims the benefit of Provisional Patent Application Ser. No. 61/909,304 for "High-Temperature, High Pressure Acoustic Resonance Cell" by Blake T. Sturtevant et at, filed on Nov. 26, 2013, which applications are hereby incorporated by reference herein for all that it discloses and teaches.

STATEMENT REGARDING FEDERAL RIGHTS

This invention was made with government support under Contract No. DE-AC 52-06NA25396 awarded by the U.S. Department of Energy. The government has certain rights in the invention.

FIELD OF THE INVENTION

The present invention relates generally to measurement of the speed of sound in fluids and, more particularly, to an acoustic resonance-based apparatus effective for speed of sound measurements in fluids at high temperatures and/or high pressures.

BACKGROUND

The measurement of sound speed in a fluid as a function of both temperature and pressure is useful for the determination of accurate equations of state. Sound speeds in liquid water have been reported up to about 3.5 GPa, at temperatures up to about 100° C. using complex, custom-made measuring instruments requiring high-precision machining and fabrication, which also tend to be non-portable and largely inseparable from the test environment. That is, samples are introduced into the instrument rather than the instrument being moveable from one test environment to another. Applications requiring an apparatus for measuring sound speeds of liquids that is capable of performing high precision measurements, portable between test environments, mechanically rugged, and able to withstand high temperatures, include the characterization of Enhanced Geothermal Systems (EGS) or Hot Dry Rock (HDR) working fluids, as well as those in the oil industry. Sound speed varies with many physical parameters of a liquid such as temperature, pressure, and dissolved solid or gas content. Thus, when used with complimentary characterization tools, sound speed provides valuable information regarding the dynamics of a fluid system Greater than 97% of the land area of United States is at temperatures of less than 250° C., at depths up to 10 km, making this a good high temperature target for operation of down hole characterization instruments. While the high pressures of such environments can be accommodated by incorporating appropriately thick walls in the device packaging, at the temperatures characteristic of down hole applications, fluids in geothermal systems are chemically harsh brines which are corrosive.

Swept Frequency Acoustic Interferometry (SFAI), where acoustic resonances of a fluid-filled cavity are measured over a range of frequencies, provides information from which the fluid sound speed, attenuation, and density can be determined. Currently available SFAI resonant cavities are delicate, room temperature instruments constructed using high purity, optically polished glass, which are excited using commercially available broadband transducers limited to operation near room temperature.

SUMMARY OF THE INVENTION

Embodiments of the present invention overcome the disadvantages and limitations of the prior art by providing an apparatus for SFAI measurements on high temperature and/or high pressure fluids (HTP-SFAI).

Another object of embodiments of the present invention is to provide an apparatus for HTP-SFAI measurements on fluids capable of operation up to about 250° C.

Yet another object of embodiments of the present invention is to provide an apparatus for HTP-SFAI measurements on fluids capable of operation up to about 250° C. and having a precision better than 0.1%.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the high-temperature, high-pressure acoustic resonance cell hereof includes: a first piezoelectric transducer; a first enclosure effective for protecting the first transducer from mechanically and chemically harsh environments, the first enclosure having a first side with a flat exterior surface and a flat interior surface parallel thereto, and wherein the first transducer is acoustically coupled to the interior surface of the first side; a second piezoelectric transducer; a second enclosure effective for protecting the second transducer from mechanically and chemically harsh environments, the second enclosure having a second side with a flat exterior surface and a flat interior surface parallel thereto, wherein the second transducer is acoustically coupled to the interior surface of the second side, and wherein the exterior surface of the first side of said first enclosure and the exterior surface of the second side of the second enclosure are parallel and spaced apart a selected distance, forming thereby a volume; a spacer member for establishing and maintaining the selected distance and parallel disposition of the first side and the second side; a signal generator for supplying a chosen time-varying electrical signals to the first piezoelectric transducer; a signal gain and phase analyzer for receiving electrical signals from the second transducer; and a processor for processing the received electrical signals from the signal gain and phase analyzer, and for controlling the signal generator.

In another aspect of the invention, and in accordance with its objects and purposes, the high-temperature, high-pressure acoustic resonance cell hereof includes: a piezoelectric transducer; an enclosure effective for protecting the transducer from mechanically and chemically harsh environments, the enclosure having a first side with a flat exterior surface and a flat interior surface parallel thereto, and wherein the transducer is acoustically coupled to the interior surface of the first side; a flat reflecting surface, wherein the exterior surface of the first side of the enclosure and the reflecting surface are parallel and spaced apart a selected distance, forming thereby a volume; a spacer for establishing and maintaining the selected distance and the parallel disposition of the first side and the reflective surface; a signal generator for supplying a chosen time-varying electrical signals to the first piezoelectric transducer; an impedance analyzer for measuring the electrical impedance of the transducer; and a processor for processing the measured electrical impedance of the transducer, and for controlling the signal generator.

Benefits and advantages of embodiments of the present invention include, but are not limited to, providing an apparatus for measuring the speed of sound of fluids at high temperatures and pressures in hostile environments.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of a side view of an embodiment of the acoustic resonance-based apparatus for measuring fluid properties of the present invention, showing transmitting and receiving acoustic transducers each mounted on the inside of a flat side of a protective container, wherein the flat sides are disposed on opposing sides of an open volume and have a chosen spacing therebetween, while

FIG. 3A is a schematic representation of a side view of the embodiment of the apparatus of the present invention for measuring fluid properties illustrated in FIG. 1, hereof, showing the elements of the two, spaced-apart transducer enclosures for the high temperature and high pressure acoustic resonance cell, FIG. 3B is a schematic representation of a perspective view of one of the piezoelectric transducer mounting flanges, while FIG. 3C is a schematic representation of a side view of the mounting flange illustrated in FIG. 3B.

FIG. 4A is a graph of the transmission scattering parameter, $|S_{21}|$, as a function of frequency for water at 30° C. and ambient pressure, while

DETAILED DESCRIPTION OF THE INVENTION

Figure 1A:
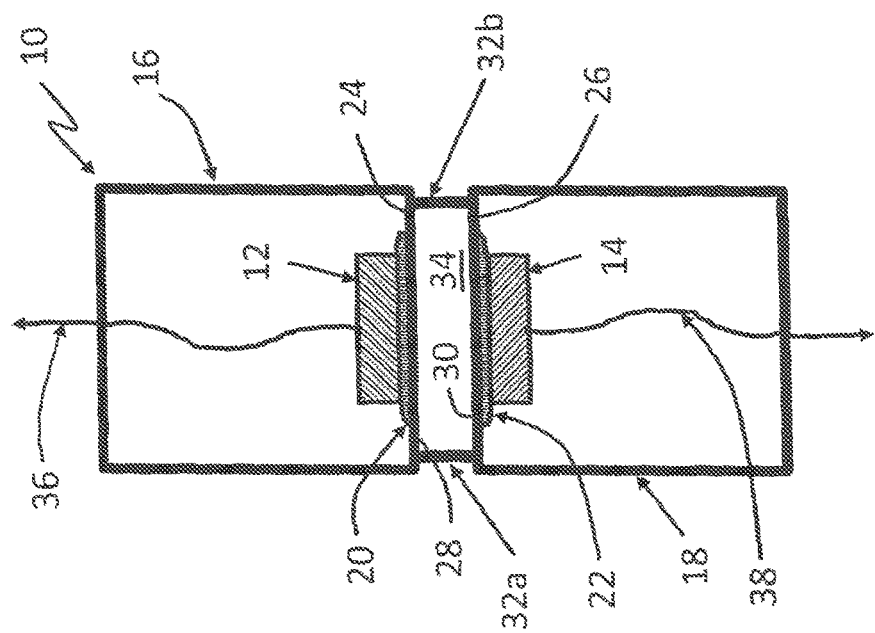

Embodiments of the present invention include an acoustic resonance cell for sound speed measurements at elevated temperatures using Swept Frequency Acoustic Interferometry, SFAI that is mechanically rugged, and offers a precision better than 0.1%. The cell described below has been repeatedly used at temperatures up to 250° C. and pressures up to 3000 psig. Applications of the present cell include the measurement of sound speed in liquids up to 250° C. for generating equations of state, and for characterizing geothermal or petroleum down hole environments, as examples. Measured sound speeds as a function of temperature and pressure using the present SFAI cell are in good agreement with internationally accepted standard values for water sound speed. It is believed by the present inventors that there are no commercially available devices that are capable of this type of measurement under high temperatures, high pressures, and in mechanically abrasive and corrosive environments.

SFAI measurements are made in a fluid-filled acoustic resonant cavity having piezoelectric transducers that are used to input and extract energy from the system. See, e.g., D. N. Sinha and G. Kaduchak, in *Experimental Methods in the Physical Sciences*, edited by H. E. B. Moises Levy and S. Richard (Academic Press, 2001), Vol. Volume 39, pp. 307-333. The frequency response of the transducer/wall/fluid-filled cavity system can be obtained by slowly and continuously changing the frequency of the input signal, and resonant frequencies where transmission is maximized, resulting from constructive interference of forward and backward traveling acoustic waves can be identified. The applied continuous wave signal can be either a square wave or a sine wave or any combination of these. The resonance condition occurs when the liquid path length, L, is an integer number of half wavelengths of the ultrasonic wave, or $\lambda n=2L/n$ where n is an integer indicating the harmonic number. Using the wave relation $c=f_n\lambda_n$, the resonant frequencies, $f_n$, can be expressed in terms the path length and the sound speed in the liquid, $c_L$: $f_n=nc_L/2L$. Measurement of L and at least two $f_n$ enables determination of the sound speed:

$$c_L = 2L\frac{df_n}{dn} \tag{1}$$

where $df_n/dn$ measures the frequency spacing between successive higher order harmonics (n, n+1, n+2, . . . ). In principle, two $f_n$ are sufficient to determine $df_n/dn=f_{n+1}-f_n$. However, greater precision in $df_n/dn$ can be achieved by considering a larger number of $f_n$.

SFAI cells do not consist solely of single fluid layers, and the walls and transducers each have resonant frequencies. At frequencies near wall or transducer resonances, energy can be coupled between the wall or transducer and the fluid, which decreases the spacing between fluid resonance peaks and affects the accurate determination of $df_n/dn$. For this reason, these frequency regions are avoided when selecting fluid peaks for calculating the speed of sound. In the EXAMPLES presented hereinbelow, the transducers have resonance frequencies at about 5 MHz, the wall resonance frequencies are spaced at approximately 800 kHz, and the desired fluid resonances are spaced at about 80 kHz.

It should be mentioned that sound attenuation may be obtained using the same data by measuring the width of each of the liquid resonance lines. From this measurement, frequency-dependent sound absorption can be determined. Sound absorption in liquids typically increases with frequency as the square of the frequency. The measured resonance width includes both the effect of absorption by the liquid, and the effect of energy loss at the metal-liquid interface due to acoustic impedance (product of density and sound speed) mismatch. The acoustic impedance mismatch effect remains constant over the entire range of the frequency sweep, except in the region where there are wall resonances. The resonance width is thus due to the sum of sound attenuation (energy loss) from acoustic impedance mismatch, and absorption by the liquid. Since the liquid density and sound speed are known, and the sound speed is determined independently, the density of the liquid can also be determined from the resonance spectrum.

Reference will now be made in detail to the present embodiments of the invention, examples of which are illustrated in the accompanying drawings. In the FIGURES, similar structure will be identified using identical reference characters. It will be understood that the FIGURES are presented for the purpose of describing particular embodiments of the invention and are not intended to limit the invention thereto. Turning now to FIG. 1, schematic representation of a side view of an embodiment of the apparatus of the present invention, 10, is shown. Transmitting piezoelectric transducer, 12, and receiving transducer, 14, may comprise lithium niobate (LiNbO$_3$) crystals having 5 MHz fundamental frequencies (Boston PiezoOptics, Inc., Bellingham, Mass.), as an example. Lithium niobate has significantly higher piezoelectric coupling than quartz and, with a Curie temperature of 1150° C., is operable at significantly higher temperatures than lead zirconium titanate piezoelectric transducers. The 36° Y-rotated cut of lithium niobate having "Z-Y'-Z" convention" Euler angles (90°, −36°, 0°) is beneficial because excitation of a pure-longitudinal acoustic mode without a shear component is desired since apparatus 10 is used to study fluids. The 10 mm diameter crystals 12 and 14 may be metalized with Cr/Au in a standard coaxial configuration to yield an active area 7 mm in diameter. Metal enclosures, 16, and, 18, were constructed using commercially available Swagelok and Conflat (CF) fittings to protect transducers 12 and 14, respectively, from mechanically and chemically harsh test environments, as will be described in more detail hereinbelow. Stainless steel fittings were employed, but other metals may provide similar protection. High-temperature acoustic coupling epoxy, 20, and 22, was used to couple transducers 12 and 14, respectively, to the interior surfaces, 24, and, 26, of flat surfaces, 28, and, 30, respectively, of the metal enclosures 16 and 18, respectively. A suitable acoustic couplant having high temperature stability, showing little degradation in preliminary furnace tests up to 400° C., and capable of maintaining a low resistivity and high efficiency of ultrasound transmission at these temperatures, was a commercially available high temperature epoxy (Epoxy H24 from Epoxy Technologies, Inc., Billerica, Mass.).

Flat surfaces 28 and 30 are spaced-apart by at least 3 spacers, shown as spacers, 32a, and, 32b, having chosen equal lengths, such that volume, 34, is formed thereby. Volume 34, which performs as an ultrasonic resonance cavity, is shown as being open such that fluids may freely flow therethrough, but may be enclosed and have inlet and outlet ports and associated valves, not shown in FIG. 1, allowing fluids to be filtered or otherwise processed before entering the volume and flowed at chosen velocities (including no velocity for the case of static measurements) therethrough. In its open construction, where volume 34 is directly exposed to the fluids undergoing measurement, apparatus 10 is insensitive to variations in pressure, because there is no differential pressure across the cell cavity. Any defect due to ambient pressure on the dimension of the spacer is negligible. High temperature signal carrying coaxial cable, 36, provides a time-varying signal from a signal generator (vector network analyzer 42, illustrated in FIG. 2, hereof) to transmitting transducer 12, while coaxial cable, 38, carries signals received on receiving transducer 14 to signal processing apparatus.

The flatness, parallelism and smoothness of surfaces 24, 26, 28, and 30, should be better than approximately 1% of a wavelength corresponding to the highest ultrasonic frequency employed. While measurements may still be possible with less-perfect features, the quality of the signal will degrade.

Figure 1B:
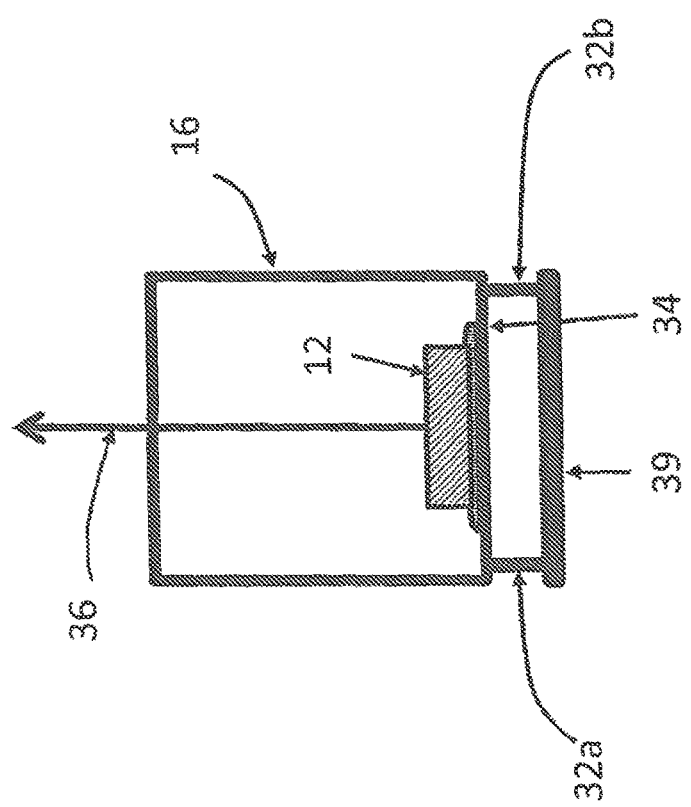
FIG. 1B is a schematic representation of a side view of another embodiment of the acoustic resonance-based apparatus for measuring fluid properties hereof, showing a transmitting and receiving acoustic transducer mounted on the inside of a flat side of a protective container, and a spaced-apart, opposing flat reflecting surface, wherein an open volume is formed therebetween.

FIG. 1B is a schematic representation of a side view of another embodiment of acoustic resonance-based apparatus 10 for measuring fluid properties hereof, showing transmitting and receiving acoustic transducer 12 mounted on the inside of flat side 28 of protective container 16, and spaced-apart, opposing flat reflecting surface, 39, wherein open volume 34 is formed therebetween. Reflecting surface 39 may comprise a metallic surface. In use, the electrical impedance of crystal 12 is measured as it is loaded by a liquid in contact therewith, since standing waves set up in the liquid in volume 34 affect the electrical impedance of crystal 12. Therefore, the same sound speed measurements can be obtained from this simplified apparatus, although the data quality for the transmission measurements has been found to be much higher.

Figure 2:
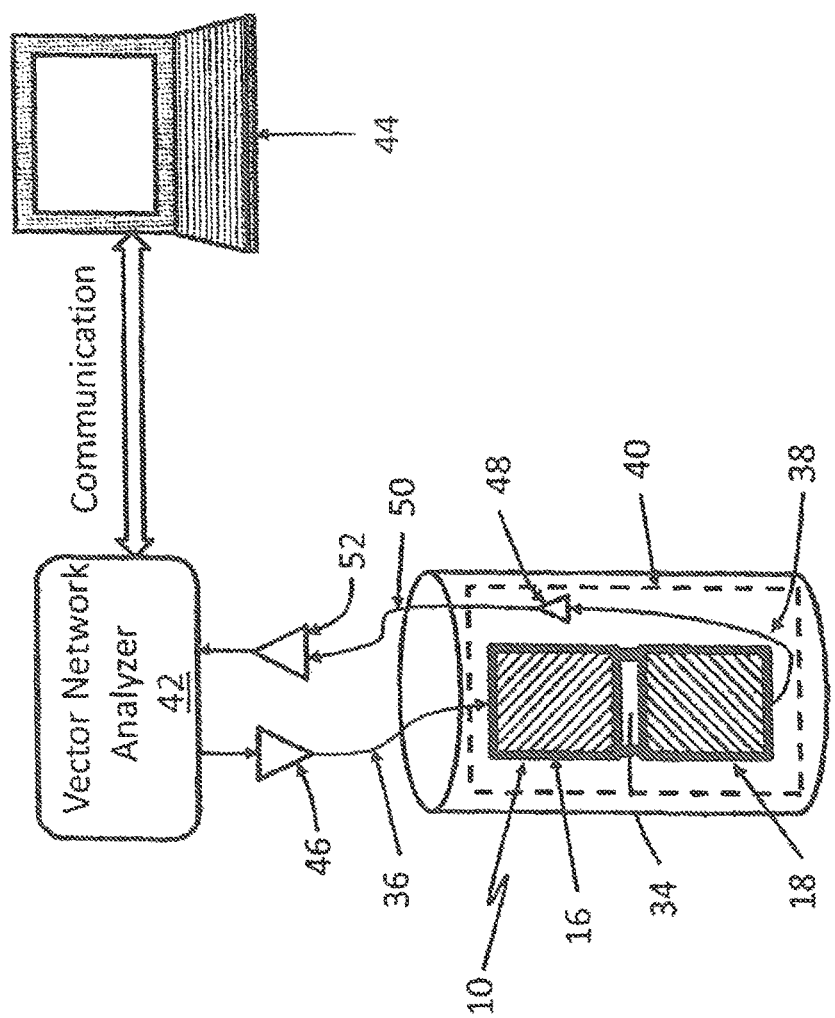
FIG. 2 is a schematic representation of a side view of the apparatus for measuring fluid properties illustrated in FIG. 1, hereof, showing the apparatus inserted into a potentially thermally, chemically and/or mechanically hostile environment as may exist for below ground applications, surrounded by a filter/mesh cage for keeping particulate matter out of resonance cavity, and coaxial cables for powering the transmitting transducer and for directing the signals received by the receiving transducer to the surface where they can be detected and digitized in the vector network analyzer, which also functions as a signal generator, from where they are directed to a processor for analysis and display of data.

FIG. 2 is schematic representation of apparatus 10 inserted into a thermally, chemically and/or mechanically hostile environment, for measuring fluid properties, surrounded by filter/mesh cage, 40, for keeping particulate matter and other solids out of resonance cavity 34. Apparatus 10 may be located at depths greater than 10,000 feet below the earth's surface for making such measurements. Coaxial cable 36 transmits a chosen signal from vector network analyzer, 42, that generates a linearly variable frequency as a function of time, and is controlled by processor, 44, which is amplified by power amplifier, 46, to transmitter transducer 12. Receiver transducer 14 receives resonance signals from resonance cavity 34 and transmits these through coaxial cable 38 to buffer amplifier, 48, for conditioning the signals for long distance transmission through coaxial cable, 50, to preamplifier, 52. Preamplifier 52 optimizes the signals for detection and digitization by vector network analyzer 42 from where they are directed to processor 44 for analysis.

FIG. 3A is a schematic representation of a side view of an assembled apparatus 10 including the spaced-apart enclosures 16 and 18 for each of the transmitting and receiving transducers 12 and 14, respectively. Illustrated are metal enclosures 16 and 18 of apparatus 10 constructed from modified, commercial vacuum fittings. Wells, 54a, and, 54b, each having a diameter of 12.5 mm, a depth of 3.2 mm, and a smooth bottom surface bored in faces 24 and 26, respectively, parallel to front faces, 28 and 30, respectively, of 1 and ⅓" diameter Conflat blank flanges (CF), 56*a*, and, 56*b*, respectively to within 25 μm, to accommodate one 10 mm diameter, 5 MHz, 36° Y-rotated lithium niobate transducer (12, 14) glued to the flange with Epotek high temperature epoxy (H24). The sound waves from the transducer crystals pass through a ⅛$^{th}$ inch thick wall. High temperature (~600° C.) stainless steel-sheathed coaxial cables 36 and 38 (THERMOCOAX, Inc.) used to transmit the signals into and out of the enclosure passes through 5/64"-0.75" Swagelok reducing unions, 58*a* and 58*b*, respectively, which make high-pressure, high-temperature seals both to cables 36 and 38, and to 1 and ⅓" Conflat half-nipples, 60*a*, and, 60*b*, respectively. Because the coaxial cable is rigid, flexible Kapton insulated wires, 62*a*, and, 62*b*, were used to electrically connect the coaxial center conductor to transducer 12 using a high-temperature silver-filled epoxy (E4110-LV, from Epoxy Technology, Inc.). The flexibility of these wires allows the Swagelok and Conflat assembly to be sealed after electrical connections have been made.

CF blank flange 56*a* was fastened to CF half nipple 60*a*, using six ¾" long bolts, not shown in FIG. 3A, while CF blank flange 56*b* was fastened to CF half nipple, again with a copper sealing gasket, using three ¾" long bolts, not shown in FIG. 3A, and three bolts which incorporate spacers, designated as 32*a* and 32*b*, the third spacer located behind apparatus 10 (that is, positioned at 120°). Assembled transducer enclosures 16 and 18 were deployed facing each other with front faces 28 and 30 of CF blank flanges 56*a* and 56*b*, respectively, defining the boundaries of the SFAI cell volume 34. The heads of the three bolts, not shown in FIG. 3A, and stainless steel spacers 32, positioned at 120° apart, define the length of the resonant cavity as L=8.848 mm. The overall length of fluid measurement cell 10 was 14 cm when opposing enclosures 56*a* and 56*b* were secured together using four bolts, shown as bolts, 64*a*, and, 64*b*, having nuts, 66*a*, and, 66*b*, respectively, holding square plates, 68*a*, and, 68*b*, respectively, adapted to capture CF half-nipples 60*a* and 60*b*, respectively. In this manner, the transducer crystals are completely protected.

FIG. 3B is a schematic representation of a perspective view of one of the piezoelectric transducer mounting flanges, while FIG. 3C is a schematic representation of a side view of the mounting flange illustrated in FIG. 3B. Shown in FIG. 3C is copper gasket, 70, capable of withstanding >250° C. used to seal flange 56*a* to Conflat half-nipple 60*a*, with a similar gasket, not shown in FIG. 3C, for sealing flange 56*b* to Conflat half-nipple 60*b*.

A pressure vessel rated to 500° C. and 5000 PSI (model #4681, Parr Instrument Company, Moline, Ill.) was used as a test environment for demonstrating the measurement cell. The 1 L volume of the pressure vessel was filled with 700 mL of distilled, degassed water. The measurement cell itself occupies a volume of ~100 mL and the remaining ~200 mL headspace consisted of air. The signal-carrying coaxial cables were sealed to the pressure vessel using Grafoil gland compression fittings (MHM2 series, Conax Technologies, Buffalo, N.Y.). A furnace heater and temperature controller were used to establish desired temperatures, and vessel internal pressure was controlled independently of temperature by pressurizing the headspace. A pressure amplifier with a 30:1 piston head area ratio (Model: AAD-30, Haskel International, Inc., Burbank, Calif.) was used to enable repeated testing up to 3000 psig. The temperature inside the water test fluid was monitored with an accuracy of ±1.1° C. or 0.4% of the reading (whichever was greater) and a precision of ±0.1° C. using a type-J thermocouple (Model M8MJSS-M2-U-250, Omega Engineering, Inc.). The system pressure was measured to an accuracy of ±13 psi using a pressure transducer with a 0-5000 psig range (Model PX309-5KG5V, Omega Engineering, Inc.). A vector network analyzer (Model Bode 100, OMICRON electronics Corp. USA, Houston Tex.) was used to measure the signal transmission characteristics of the fluid-filled cell, also termed the $S_{21}$ forward transmission scattering parameter. The scattering parameters $S_{21}$ and $S_{11}$ are used to quantify the transmitted power and reflected power, respectively, as a fraction of the power input into the measurement cell.

Having generally described embodiments of the present invention, the following EXAMPLES provide additional details.

EXAMPLE 1

Figure 4A:
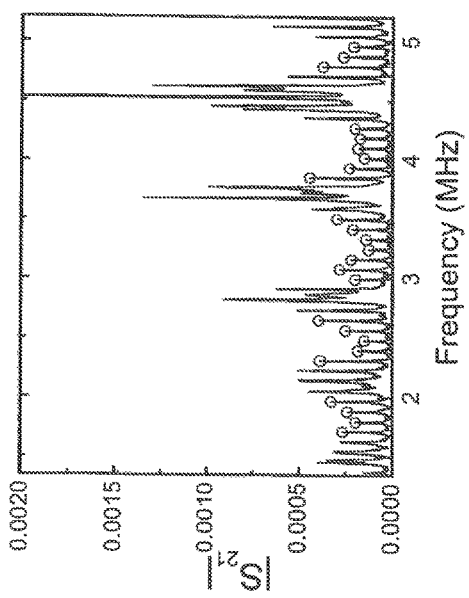
Figure 4B:
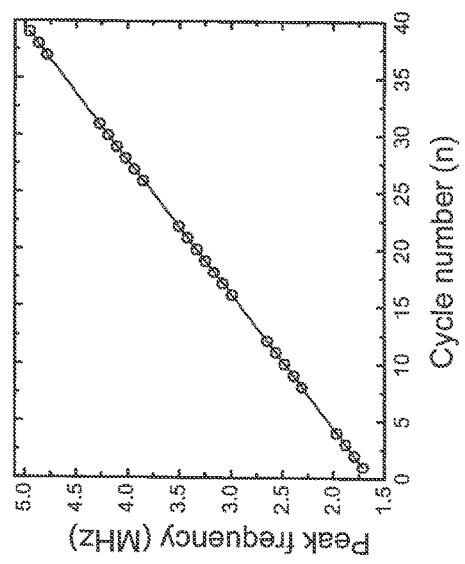
FIG. 4B is a graph of the center frequencies indicated with open circles from regions not affected by wall or transducer resonances, as a function of cycle number, for determining $df_n/dn$.

Determining Sound Speed from $|S_{21}|$ Transmission Spectrum:

FIG. 4A is a graph of the transmission scattering parameter, $|S_{21}|$, as a function of frequency for water, collected at 30° C. and ambient pressure. A number of these resonances are chosen because they are separated from wall and transducer resonances, and are indicated with circles. To determine $df_n/dn$, the frequencies of the resonances identified in FIG. 4A are plotted against 'cycle number', taking into account those cycles for which resonances are not recorded (specifically: n=[5-7, 13-15, 22-25, 32-36]) as shown in FIG. 4B. For the purpose of determining sound speed, it is only necessary to know n in a relative and not an absolute sense since the slope of $f_n$ vs. n is the only quantity of interest. A linear least-squares fit, shown in FIG. 4B, was performed using the 25 resonances shown in FIG. 4A to yield $df_n/dn = 85.408 \pm 0.033$ kHz. Using the measured path length, L=8.848 mm, the sound speed is determined to be 1511.4±0.6 m/s. The standard deviation, σ=33 Hz, of the linear fit slope contributes to a relative uncertainty in sound speed of 0.04%.

EXAMPLE 2

Sound Speed as a Function of Pressure at 31° C.:

The first set of data presented here was collected at 30.9±0.5° C. at 20 pressures between ambient pressure and 3000 psig. TABLE I presents the determined sound speed vs. pressure data along with the sound speed calculated by the IAPWS-IF97 standard. See, e.g., W. Wagner and H.-J. Kretzschmar, *International Steam Tables: Properties of Water and Steam Based on the Industrial Formulation IAPWS-IF97*, second ed. (Springer-Verlag, Berlin, 2008).

The IAPWS-IF97 sound speeds are not experimental points, but are calculated from the equation of state for water given in W. Wagner et al., supra. The equations used in these calculations are also found in W. Wagner et al., supra, while the full set of experimental thermodynamic data upon which the equation of state is based are described in W. Wagner and A. Pruss, J. Phys. Chem. Ref. Data 31 (2), 387-535 (2002). The IAPWS calculations are used for comparison since there is no previous single set of direct sound speed measurements for temperature and pressure range presently measured. The sound speed was determined from a measured transmission spectrum, from which $df_n/dn$ was calculated as described hereinabove. The path length, L=8.848 mm, was calibrated using the known sound speed in deionized and degassed 25° C. water as a standard. In the present measurements, pressure changes were accompanied by small changes in temperature due to compression or expansion of the gas in the headspace of the vessel. At about 30° C., an increase in temperature of 1° C. has the same effect on the sound speed in water as increasing the pressure by 200 psi, and the slightly different temperatures were corrected for. In all cases, the determined sound speeds agree with the IAPWS-IF97 values to within 0.5 m/s. This agreement provides a validation for the measurement precision determined by the linear fit of $f_n$ vs. n.

TABLE I

Comparison of experimentally determined and predicted sound speed

| Temp (° C.) | Pressure (psig) | Determined Sound Speed (m/s) | Predicted Sound Speed (m/s) Ref [18] |
|---|---|---|---|
| 30.4 | 7 | 1511.8 | 1512.0 |
| 30.4 | 195 | 1513.7 | 1514.0 |
| 30.5 | 397 | 1516.1 | 1516.3 |
| 30.4 | 600 | 1518.4 | 1518.5 |
| 30.5 | 797 | 1521.0 | 1520.9 |
| 30.6 | 999 | 1523.0 | 1523.4 |
| 30.6 | 1205 | 1525.4 | 1525.6 |
| 30.7 | 1400 | 1528.1 | 1528.0 |
| 30.7 | 1606 | 1530.2 | 1530.3 |
| 30.8 | 1798 | 1532.9 | 1532.7 |
| 30.9 | 1997 | 1534.8 | 1535.1 |
| 31 | 2195 | 1537.2 | 1537.6 |
| 31.2 | 2402 | 1540.1 | 1540.4 |
| 31.3 | 2602 | 1543.0 | 1542.8 |
| 31.4 | 2813 | 1544.9 | 1545.4 |
| 31.4 | 2995 | 1547.2 | 1547.5 |

EXAMPLE 3

Figure 5:
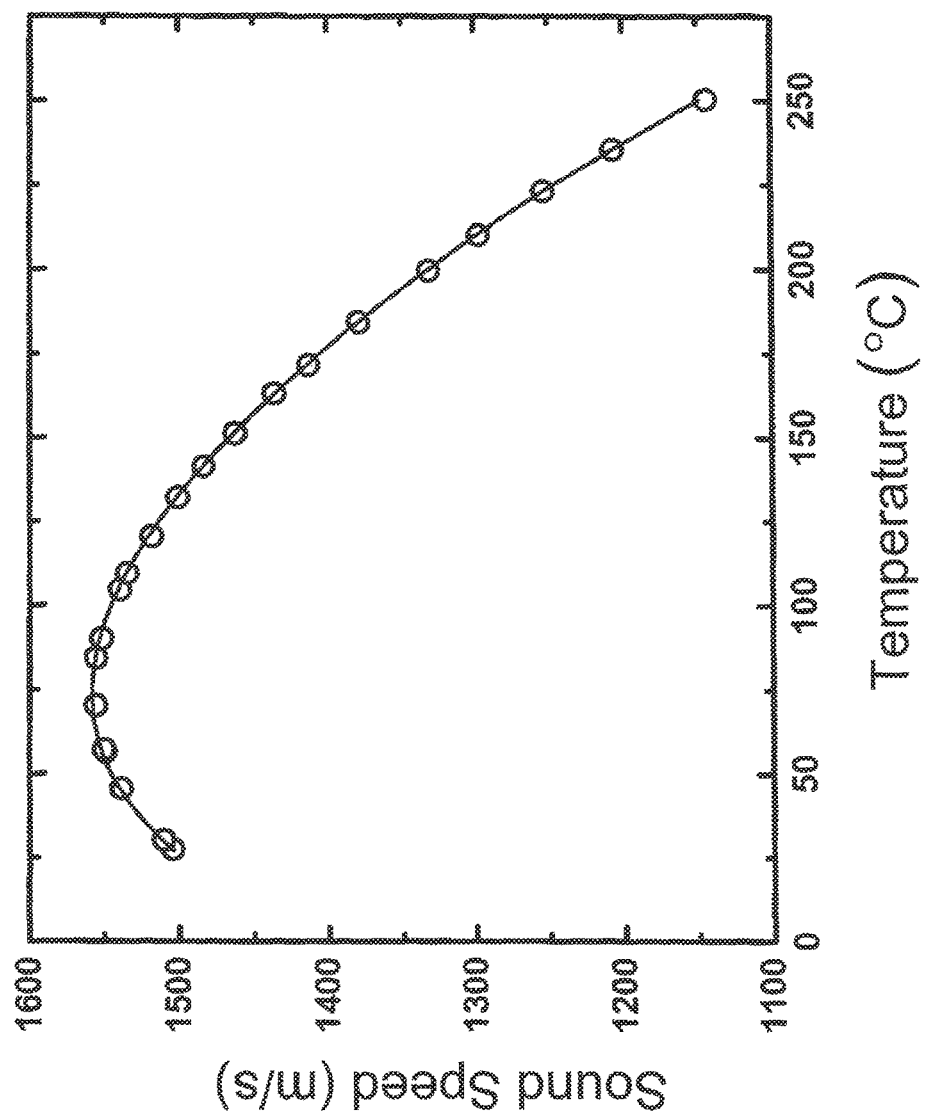
FIG. 5 is a graph of the speed of sound in water as a function of temperature up to 250.4° C. along the liquid-vapor coexistence curve, where the 22 open circles represent sound speeds determined from SFAI measurements employing the apparatus of the present invention, and the solid trace corresponds to calculated sound speeds.

Liquid Water Sound Speeds Measured Along the Liquid-Vapor Coexistence Curve:

The second set of data presented here was collected in liquid water at 22 temperatures between laboratory ambient and 250° C., at pressures corresponding to the liquid-vapor coexistence line. At each temperature, the sound speed was determined using the procedure described hereinabove. The path length, L, was corrected for changes in temperature using a calibrated 25° C. value of L and a linear thermal coefficient of expansion for stainless steel of $16 \times 10^{-6}/°$ C. The measured data show very good agreement with the IAPWS-IF97 predicted sound speeds (Wagner et al., supra) as can be seen from FIG. 5 and TABLE II. For all points, the discrepancy between the measured and IAPWS-IF97 predicted sound speed is less than 0.3% (~3 m/s). Discrepancies are likely attributed to errors in the temperature measurements by the thermocouple. At higher temperatures, small errors in temperature can have a significant impact on the sound speed of water. For example, at 220° C., a change in temperature of 1° C. leads to a 3.6 m/s change in water sound speed. The inability to measure temperature to better than about one degree Celsius does not affect the measurement precision of the present HTP-SFAI measurement cell. As indicated above and in TABLE I, the precision of the measurement cell is better estimated by the standard deviation in $df_n/dn$, and is typically in the range of 0.5 m/s or less than 0.1%.

EXAMPLE 4

Figure 6:
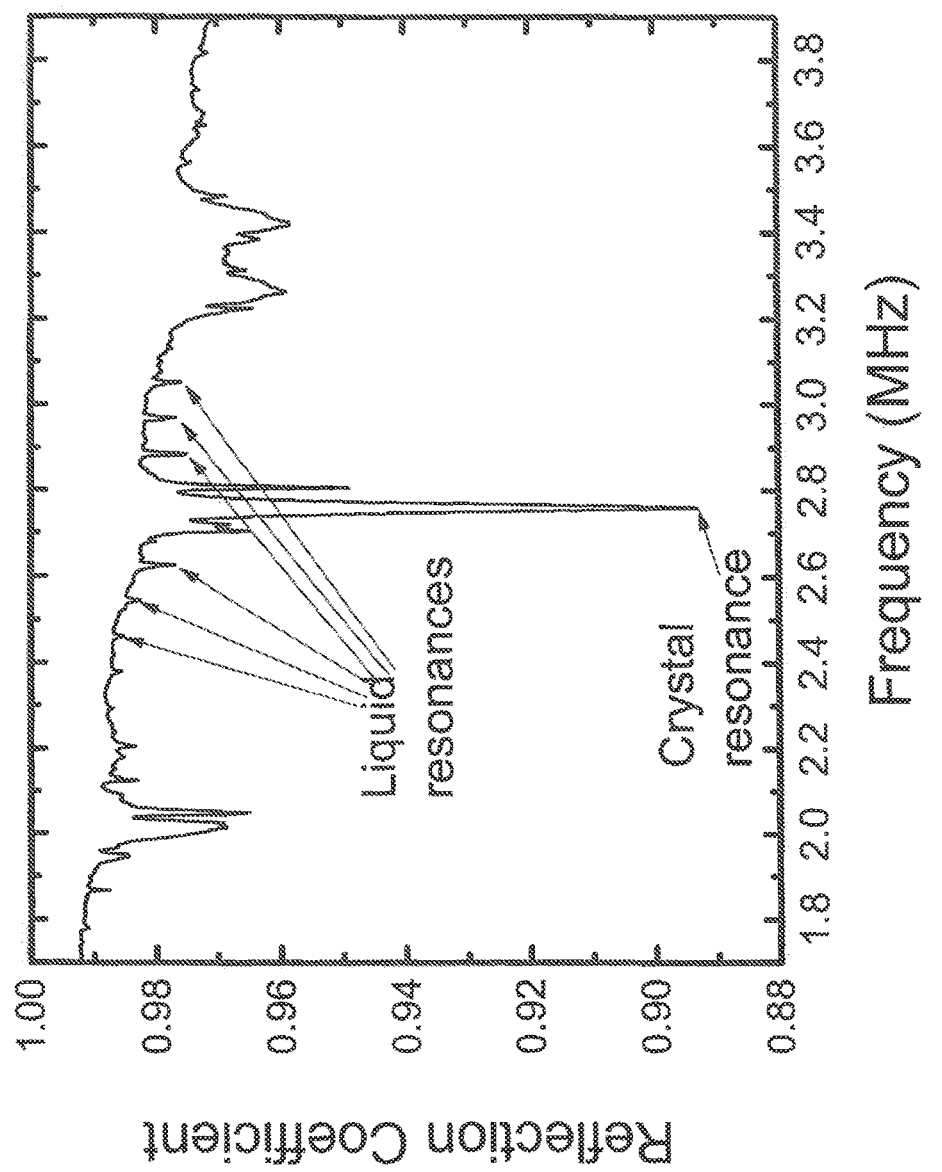
FIG. 6 is a graph of the reflection coefficient (scattering parameter $[S_{11}]$) as a function of frequency using the reflection embodiment of the present apparatus illustrated in FIG. 1B hereof for pure water at laboratory ambient temperature and pressure.

Measurements Using the Reflection Embodiment:

FIG. 6 is a graph of the reflection coefficient (scattering parameter $[S_{11}]$) as a function of frequency using the reflection embodiment of the present apparatus illustrated in FIG. 1B hereof for pure water at laboratory ambient temperature (22° C.) and pressure (12 psi).

TABLE II

Experimentally determined and predicted water sound speeds along the liquid-vapor coexistence curve

| Temperature (° C.) | Determined Sound Speed (m/s) | Predicted Sound Speed (m/s) Ref [18] | Difference [a] (%) |
|---|---|---|---|
| 27.5 | 1504.4 | 1504.7 | −0.02 |
| 30.3 | 1510.2 | 1511.5 | −0.09 |
| 45.5 | 1538.5 | 1539.6 | −0.07 |
| 56.5 | 1548.7 | 1551.3 | −0.17 |
| 57.3 | 1549.9 | 1551.9 | −0.13 |
| 70.4 | 1555.2 | 1557.5 | −0.15 |
| 84.5 | 1555.0 | 1555.5 | −0.03 |
| 90.3 | 1551.1 | 1552.5 | −0.09 |
| 104.8 | 1539.1 | 1540.3 | −0.08 |
| 109.6 | 1534.3 | 1534.9 | −0.04 |
| 120.5 | 1518.0 | 1520.3 | −0.15 |
| 132.1 | 1500.6 | 1501.3 | −0.05 |
| 141.4 | 1483.4 | 1483.9 | −0.03 |
| 151.4 | 1462.1 | 1462.9 | −0.05 |
| 163.1 | 1436.0 | 1435.7 | 0.03 |
| 171.6 | 1412.9 | 1414.1 | −0.09 |
| 184.4 | 1378.7 | 1378.8 | −0.01 |
| 199.8 | 1331.1 | 1332.1 | −0.08 |
| 210.1 | 1297.1 | 1298.3 | −0.10 |
| 223.1 | 1252.8 | 1252.8 | 0.00 |
| 235.6 | 1206.2 | 1206.0 | 0.01 |
| 250.4 | 1143.6 | 1146.7 | −0.28 |

[a] Difference = 100* (Measured − Calculated)/Measured

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. A high-temperature, high-pressure acoustic resonance cell, comprising:
   a first piezoelectric transducer;
   a first enclosure effective for protecting said first transducer from mechanically and chemically harsh environments, said first enclosure having a first side with a flat exterior surface and a flat interior surface parallel thereto, and wherein said first transducer is acoustically coupled to the interior surface of the first side;
   a second piezoelectric transducer;
   a second enclosure effective for protecting said second transducer from mechanically and chemically harsh environments, said second enclosure having a second side with a flat exterior surface and a flat interior surface parallel thereto, wherein said second transducer is acoustically coupled to the interior surface of the second side, and wherein the exterior surface of the first side of said first enclosure and the exterior surface of the second side of said second enclosure are parallel and spaced apart a selected distance, forming thereby a volume;

a spacer member for establishing and maintaining the selected distance and parallel disposition of the first side and the second side, wherein the volume, when filled with a fluid, performs as an acoustic resonance cavity;

a signal generator for supplying a continuous wave electrical signal having a swept frequency over a frequency range encompassing at least two resonant frequencies of the fluid-filled volume to said first piezoelectric transducer;

a signal gain and phase analyzer for receiving electrical signals from said second transducer; and a processor for processing the received electrical signals from said signal gain and phase analyzer, and for controlling said signal generator.

2. The acoustic resonance cell of claim 1, wherein said first transducer and said second transducer comprise high-temperature transducers.

3. The acoustic resonance cell of claim 2, wherein said first transducer and said second transducer are chosen from lithium niobate and lead zirconium titanate piezoelectric transducers.

4. The acoustic resonance cell of claim 1, wherein said first transducer is acoustically coupled to the interior surface of the first side of said first enclosure using high-temperature acoustic coupling epoxy and said second transducer is acoustically coupled to the interior surface of the second side of said second enclosure using high-temperature acoustic coupling epoxy.

5. The acoustic resonance cell of claim 1, wherein said spacer member comprises at least one spacer adapted to permit fluids to freely flow through the volume, whereby pressure of the fluid in the volume is the same as pressure of the fluid outside of the volume.

6. The acoustic resonance cell of claim 5, wherein speed of sound and sound absorption in the fluid is measured.

7. The acoustic resonance cell of claim 1, further comprising a filter/mesh cage surrounding said first enclosure, said second enclosure and said spacer member, for keeping particulate matter out of the volume.

8. The acoustic resonance cell of claim 1, wherein the chosen time-varying electrical signal to said first piezoelectric transducer is chosen from sinusoidal and periodic square-wave signals.

9. The acoustic resonance cell of claim 8, wherein the chosen time-varying electrical signal is swept over a selected frequency range.

10. A high-temperature, high-pressure acoustic resonance cell, comprising:

a piezoelectric transducer;

an enclosure effective for protecting said transducer from mechanically and chemically harsh environments, said enclosure having a first side with a flat exterior surface and a flat interior surface parallel thereto, and wherein said transducer is acoustically coupled to the interior surface of the first side;

a flat reflecting surface, wherein the exterior surface of the first side of said enclosure and the reflecting surface are parallel and spaced apart a selected distance, forming thereby a volume;

a spacer for establishing and maintaining the selected distance and parallel disposition of the first side and the reflecting surface, wherein the volume, when filled with fluid, performs as an acoustic resonance cavity;

a signal generator for supplying a continuous wave electrical signal having a swept frequency over a frequency range encompassing at least two resonant frequencies of the fluid-filled volume to said first piezoelectric transducer;

an impedance analyzer for measuring the electrical impedance of said transducer responsive to standing waves set up in the volume; and a processor for processing the measured electrical impedance of said transducer, and for controlling said signal generator.

11. The acoustic resonance cell of claim 10, wherein said transducer comprises a high-temperature transducer.

12. The acoustic resonance cell of claim 11, wherein said transducer is chosen from lithium niobate and lead zirconium titanate piezoelectric transducers.

13. The acoustic resonance cell of claim 10, wherein said transducer is acoustically coupled to the interior surface of the first side of said enclosure using high-temperature acoustic coupling epoxy.

14. The acoustic resonance cell of claim 10, wherein said spacer member comprises at least one spacer adapted to permit fluids to freely flow through the volume, whereby pressure of the fluid in the volume is the same as pressure of the fluid outside of the volume.

15. The acoustic resonance cell of claim 14, wherein speed of sound and sound absorption in the fluid is measured.

16. The acoustic resonance cell of claim 10, further comprising a filter/mesh cage surrounding said enclosure and said spacer member, for keeping particulate matter out of the volume.

17. The acoustic resonance cell of claim 10, wherein the chosen time-varying electrical signal to said first piezoelectric transducer is chosen from sinusoidal and periodic square-wave signals.

18. The acoustic resonance cell of claim 17, wherein the chosen time-varying electrical signal is swept over a selected frequency range.

* * * * *